United States Patent [19]

Maurer et al.

[11] 4,126,690
[45] Nov. 21, 1978

[54] COMBATING ARTHROPODS WITH N,N-DIMETHYL-O-[3-(SUBSTITUTED-METHYL)-PYRAZOL-5-YL]-CARBAMIC ACID ESTERS

[75] Inventors: Fritz Maurer; Hans-Jochem Riebel, both of Wuppertal; Rolf Schröder, Velbert; Ingeborg Hammann, Cologne; Bernhard Homeyer, Leverkusen; Wilhelm Stendel, Wuppertal, all of Germany

[73] Assignee: Bayer Aktiengesellschaft, Leverkusen, Germany

[21] Appl. No.: 838,425

[22] Filed: Sep. 30, 1977

[30] Foreign Application Priority Data

Oct. 2, 1976 [DE] Fed. Rep. of Germany ....... 2644588
May 11, 1977 [DE] Fed. Rep. of Germany ....... 2721188

[51] Int. Cl.² .................. C07D 231/22; C07D 231/20; A01N 9/22
[52] U.S. Cl. ................. 424/273 P; 548/377; 548/367
[58] Field of Search ............... 548/376, 377; 424/273 P

[56] References Cited

U.S. PATENT DOCUMENTS

| 2,681,915 | 6/1954 | Gysin et al. ................ 548/377 |
| 3,395,155 | 7/1968 | Gubler ..................... 424/273 P |

FOREIGN PATENT DOCUMENTS

| 279,553 | 3/1952 | Switzerland. |
| 281,967 | 7/1952 | Switzerland. |
| 282,655 | 8/1952 | Switzerland. |

*Primary Examiner*—Natalie Trousof
*Assistant Examiner*—Natalia Harkaway
*Attorney, Agent, or Firm*—Sprung, Felfe, Horn, Lynch & Kramer

[57] ABSTRACT

N,N-Dimethyl-O-[3-(substituted-methyl)-pyrazol-5-yl]-carbamic acid esters of the formula

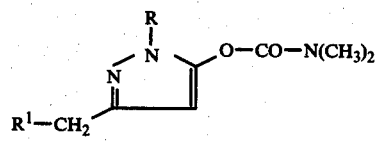

in which
R is hydrogen, alkyl, cyanoalkyl or phenyl, and
$R^1$ is alkoxy or alkylthio which possess arthropodicidal properties.

8 Claims, No Drawings

COMBATING ARTHROPODS WITH N,N-DIMETHYL-O-[3-(SUBSTITUTED-METHYL)-PYRAZOL-5-YL]-CARBAMIC ACID ESTERS

The present invention relates to and has for its objects the provision of particular new N,N-dimethyl-O-[3-(substituted-methyl)-pyrazol-5-yl]-carbamic acid esters which possess arthropodicidal properties, active compositions in the form of mixtures of such compounds with solid and liquid dispersible carrier vehicles, and methods for producing such compounds and for using such compounds in a new way especially for combating pests, e.g. arthropods, with other and further objects becoming apparent from a study of the within specification and accompanying examples.

It has been disclosed in Swiss Patent Specifications 282,655, 281,967 and 279,553 that certain N,N-dimethyl-O-pyrazolyl-carbamic acid esters, for example N,N-dimethyl-O-[1-phenyl-3-methyl-(Compound B) and 1-isopropyl-3-methyl-pyrazol-5-yl]-carbamic acid ester (Compound A), possess insecticidal properties.

The present invention now provides, as new compounds, the N,N-dimethyl-O-pyrazolyl-carbamic acid esters of the general formula

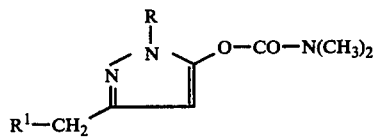

in which
R represents hydrogen, alkyl, cyanoalkyl or phenyl, and
$R^1$ represents alkoxy or alkylthio.

Preferably, R represents hydrogen, phenyl, straight-chain or branched alkyl with 1 to 8 (especially 1 to 5 or 6) carbon atoms or cyanoalkyl with 1 to 4 (especially 1 or 2) carbon atoms in the alkyl radical and $R^1$ represents straight-chain or branched alkoxy or alkylthio each with 1 to 6 (especially 1 to 4) carbon atoms.

Surprisingly, the N,N-dimethyl-O-pyrazolyl-carbamic acid esters (I) according to the invention exhibit a substantially better insecticidal action than the previously known O-pyrazolyl-carbamic acid esters of analogous structure and of the same type of action. The compounds according to the invention thus represent a genuine enrichment of the art.

The invention also provides a process for the preparation of an N,N-dimethyl-O-pyrazolyl-carbamic acid ester of the formula (I) in which a 5-hydroxypyrazole of the general formula

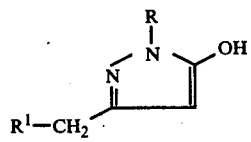

in which
R and $R^1$ have the above-mentioned meanings, is reacted, either as such in the presence of an acid acceptor or in the form of an alkali metal salt, alkaline earth metal salt of ammonium salt, with N,N-dimethylcarbamic acid chloride, of the formula $$Cl-CO-N(CH_3)_2 \quad (III),$$

in the presence of a solvent or diluent.

If 1-ethyl-3-n-propoxymethyl-5-hydroxy-pyrazole and N,N-dimethylcarbamic acid chloride are used as starting materials, the course of the reaction can be represented by the following equation:

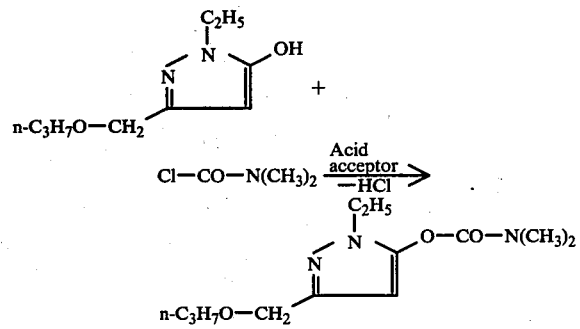

The 5-hydroxy-pyrazoles (II) to be used as starting materials can be prepared in accordance with processes known from the literature, by reacting halogenoacetoacetic acid alkyl esters with an alcoholate or alkylmercaptide and cyclizing the resulting alkoxy- or alkylthio-acetoacetic acid alkyl esters with hydrazine drivatives.

The following may be mentioned as individual examples of the above: 3-methoxymethyl-, 3-ethoxymethyl-, 3-n-propoxymethyl-, 3-iso-propoxymethyl-, 3-n-butoxymethyl-, 3-iso-butoxymethyl-, 3-sec.-butoxymethyl-, 3-methylthiomethyl-, 3-ethylthiomethyl-, 3-n-propylthiomethyl-, 3-iso-propylthiomethyl-, 3-n-butylthiomethyl-, 3-iso-butylthiomethyl- and 3-sec.-butylthiomethyl-5-hydroxy-pyrazole, 1-phenyl-3-methoxymethyl-, 1-phenyl-3-ethoxymethyl-, 1-phenyl-3-n-propoxymethyl-, 1-phenyl-3-iso-propoxymethyl-, 1-phenyl-3-n-butoxymethyl-, 1-phenyl-3-iso-butoxymethyl-, 1-phenyl-3-sec.-butoxymethyl-, 1-phenyl-3-methylthiomethyl-, 1-phenyl-3-ethylthiomethyl-, 1-phenyl-3-n-propylthiomethyl-, 1-phenyl-3-iso-propylthiomethyl-, 1-phenyl-3-n-butylthiomethyl-, 1-phenyl-3-iso-butylthiomethyl- and 1-phenyl-3-sec.-butylthiomethyl-5-hydroxy-pyrazole, 1-methyl-3-methoxymethyl-, 1-methyl-3-ethoxymethyl-, 1-methyl-3-n-propoxymethyl-, 1-methyl-3-iso-propoxymethyl-, 1-methyl-3-n-butoxymethyl-, 1-methyl-3-iso-butoxymethyl-, 1-methyl-3-sec.-butoxymethyl-, 1-methyl-3-methylthiomethyl-, 1-methyl-3-ethylthiomethyl-, 1-methyl-3-n-propylthiomethyl-, 1-methyl-3-iso-propylthiomethyl-, 1-methyl-3-n-butylthiomethyl-, 1-methyl-3-iso-butylthiomethyl- and 1-methyl-3-sec.-butylthiomethyl-5-hydroxy-pyrazole, 1-ethyl-3-methoxymethyl-, 1-ethyl-3-ethoxymethyl-, 1-ethyl-3-n-propoxymethyl-, 1-ethyl-3-iso-propoxymethyl-, 1-ethyl-3-n-butoxymethyl-, 1-ethyl-3-iso-butoxymethyl-, 1-ethyl-3-sec.-butoxymethyl-, 1-ethyl-3-methylthiomethyl-, 1-ethyl-3-ethylthiomethyl-, 1-ethyl-3-n-propylthiomethyl-, 1-ethyl-3-isopropylthiomethyl-, 1-ethyl-3-butylthiomethyl-, 1-ethyl-3-isobutylthiomethyl- and 1-ethyl-3-sec.-butylthiomethyl-5-hydroxy-pyrazole, 1-n-propyl-3-methoxymethyl-, 1-n-propyl-3-ethoxymethyl-, 1-n-propyl-3-n-propoxymethyl-, 1-n-propyl-3-iso-propoxymethyl-, 1-n-propyl-3-n-butoxymethyl-, 1-n-propyl-3-iso-butoxymethyl-, 1-n-propyl-3-sec.-butoxymethyl-, 1-n-propyl-3-methylthiomethyl-, 1-n-propyl-3-ethylthiomethyl-, 1-n-propyl-3-n-propylthiomethyl-, 1-n-propyl-3-iso-propylthiomethyl-, 1-n- propyl-3-n-butylthiomethyl-, 1-n-propyl-3-iso-butylthiomethyl-, and 1-n-propyl-3-sec.-butylthiomethyl-5-hydroxy-pyrazole, 1-iso-propyl-3-methoxymethyl-, 1-iso-propyl-3-ethoxymethyl-, 1-iso-propyl-3-n-propoxymethyl-, 1-iso-propyl-3-iso-propoxymethyl-, 1-iso-propyl-3-n-butoxymethyl-, 1-iso-propyl-3-iso-butoxymethyl-, 1-iso-propyl-3-sec.-butoxymethyl-, 1-iso-propyl-3-methylthiomethyl-, 1-iso-propyl-3-ethylthiomethyl-, 1-iso-propyl-3-n-propylthiomethyl-, 1-iso-propyl-3-iso-propylthiomethyl-, 1-iso-propyl-3-n-butylthiomethyl-, 1-iso-propyl-3-n-butylthiomethyl-, 1-iso-propyl-3-iso-butylthiomethyl- and 1-iso-propyl-3-sec.-butylthiomethyl-5-hydroxy-pyrazole, 1-n-butyl-3-methoxymethyl-, 1-n-butyl-3-ethoxymethyl-, 1-n-butyl-3-n-propoxymethyl, 1-n-butyl-3-iso-propoxymethyl-, 1-n-butyl-3-n-butoxymethyl-, 1-n-butyl-3-iso-butoxymethyl-, 1-n-butyl-3-sec.-butoxymethyl-, 1-n-butyl-3-methylthiomethyl-, 1-n-butyl-3-ethylthiomethyl-, 1-n-butyl-3-n-propylthiomethyl-, 1-n-butyl-3-iso-propylthiomethyl-, 1-n-butyl-3-n-butylthiomethyl-, 1-n-butyl-3-iso-butylthiomethyl- and 1-n-butyl-3-sec.-butylthiomethyl-5-hydroxy-pyrazole, 1-sec.-butyl-3-methoxymethyl-, 1-sec.-butyl-3-ethoxymethyl-, 1-sec.-butyl-3-n-propoxymethyl-, 1-sec.-butyl-3-iso-propoxymethyl-, 1-sec.-butyl-3-n-butoxymethyl-, 1-sec.-butyl-3-iso-butoxymethyl-, 1-sec.-butyl-3-sec.-butoxymethyl-, 1-sec.-butyl-3-methylthiomethyl-, 1-sec.-butyl-3-ethylthiomethyl-, 1-sec.-butyl-3-n-propylthiomethyl-, 1-sec.-butyl-3-iso-propylthiomethyl-, 1-sec.-butyl-3-n-butylthiomethyl-, 1-sec.-butyl-3-iso-butylthiomethyl- and 1-sec.butyl-3-sec.-butylthiomethyl-5-hydroxy-pyrazole, 1-iso-butyl-3-methoxymethyl-, 1-iso-butyl-3-ethoxymethyl-, 1-iso-butyl-3-n-propoxymethyl-, 1-iso-butyl-3-iso-propoxymethyl-, 1-iso-butyl-3-n-butoxymethyl-, 1-iso-butyl-3-iso-butoxymethyl-, 1-iso-butyl-3-sec.-butoxymethyl-, 1-iso-butyl-3-methyl-thiomethyl-, 1-iso-butyl-3-ethylthiomethyl-, 1-iso-butyl-3-n-propylthiomethyl-, 1-iso-butyl-3-iso-propylthiomethyl-, 1-iso-butyl-3-n-butylthiomethyl, 1-iso-butyl-3-iso-butyl-thiomethyl- and 1-iso-butyl-3-sec.-butylthiomethyl-5-hydroxy-pyrazole, 1-tert.-butyl-3-methoxymethyl-, 1-tert.-butyl-3-ethoxymethyl-, 1-tert.-butyl-3-n-propoxymethyl-, 1-tert.-butyl-3-iso-propoxymethyl-, 1-tert.-butyl-3-n-butoxymethyl-, 1-tert.-butyl-3-iso-butoxymethyl-, 1-tert.-butyl-3-sec.-butoxymethyl-, 1-tert.-butyl-3-methylthiomethyl-, 1-tert.-butyl-3-ethylthiomethyl-, 1-tert.-butyl-3-n-propylthiomethyl-, 1-tert.-butyl-3-iso-propylthiomethyl-, 1-tert.-butyl-3-n-butylthiomethyl-, 1-tert.-butyl-3-iso-butylthiomethyl- and 1-tert.-butyl-3-sec.-butylthiomethyl-5-hydroxy-pyrazole, 1-cyanomethyl-3-methoxymethyl-, 1-cyanomethyl-3-ethoxymethyl-, 1-cyanomethyl-3-n-propoxymethyl-, 1-cyanomethyl-3-iso-propoxymethyl-, 1-cyanomethyl-3-n-butoxymethyl-, 1-cyanomethyl-3-iso-butoxymethyl-, 1-cyanomethyl-3-sec.-butoxymethyl-, 1-cyanomethyl-3-methylthiomethyl-, 1-cyanomethyl-3-ethylthiomethyl-, 1-cyanomethyl-3-n-propylthiomethyl-, 1-cyanomethyl-3-iso-propylthiomethyl-, 1-cyanomethyl-3-n-butylthiomethyl-, 1-cyanomethyl-3-iso-butylthiomethyl- and 1-cyanomethyl-3-sec.-butyl-thiomethyl-5-hydroxy-pyrazole and 1-(2-cyanoethyl)-3-methoxymethyl-, 1-(2-cyanoethyl)-3-ethoxymethyl-, 1-(2-cyanoethyl)-3-n-propoxymethyl-, 1-(2-cyanoethyl)-3-iso-propoxymethyl-, 1-(2-cyanoethyl)-3-n-butoxymethyl-, 1-(2-cyanoethyl)-3-iso-butoxymethyl-, 1-(2-cyanoethyl)-3-sec.-butoxymethyl-, 1-(2-cyanoethyl)-3-methylthiomethyl-, 1-(2-cyanoethyl)-3-ethylthiomethyl-, 1-(2-cyanoethyl)-3-n-propylthiomethyl-, 1-(2-cyanoethyl)-3-iso-propylthiomethyl-, 1-(2-cyanoethyl)-3-n-butylthiomethyl-, 1-(2-cyanoethyl)-3-iso-butylthiomethyl- and 1-(2-cyanoethyl)-3-sec.-butylthiomethyl-5-hydroxy-pyrazole.

The N,N-dimethyl-carbamic acid chloride (III) also to be used as a starting material is known from the literature and can readily be prepared in accordance with generally customary processes.

The process for the preparation of the compounds according to the invention is carried out in the presence of a suitable solvent or diluent. Virtually all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methylisopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate, ethylate and tert.-butylate, have proved particularly suitable, as have aliphatic, aromatic or heterocyclic amines, for example triethylamine, trimethylamine, dimethylaniline, dimethylbenzylamine and pyridine.

The reaction temperature can be varied within a substantial range. In general, the reaction is carried out at from $-10°$ to $+80°$ C, preferably at from 20° to 60° C.

In general, the reaction is allowed to take place under normal pressure.

To carry out the process, the starting components are in most cases employed in stoichiometric amounts. An excess of one or other reactant produces no significant advantages. Preferably, the 5-hydroxy-pyrazole component and the acid acceptor are initially introduced into a solvent and the suspension is stirred for one hour at an elevated temperature and then cooled, after which the carbamic acid chloride is added dropwise. After stirring the mixture further for from one to several hours at an elevated temperature, the reaction solution is diluted with water and extracted by shaking with an organic solvent. The organic phase is separated off and then worked up in the usual manner by drying and distilling off the solvent.

The new compounds are frequently obtained in the form of oils which in most cases cannot be distilled without decomposition, but are freed from the last volatile constituents by so-called "slight distillation", that is to say by prolonged heating under reduced pressure to moderately elevated temperatures, and are purified in this way. They are characterized by the refractive index. Some compounds are obtained in a crystalline form and are characterized by their melting point.

As already mentioned, the N,N-dimethyl-O-pyrazolylcarbamic acid esters according to the invention are distinguished by an excellent insecticidal activity.

The active compounds are well tolerated by plants, have a favorable level of toxicity to warm-blooded animals, and can be used for combating arthropod pests, especially insects, which are encountered in agriculture, in forestry, in the protection of stored products and of materials, and in the hygiene field. They are active against normally sensitive and resistant species and against all or some stages of development. The above-mentioned pests include:

from the class of the *Isopoda*, for example *Oniscus asellus, Armadillidium vulgare* and *Porcellio scaber;* from the class of the *Diplopoda*, for example *Blaniulus guttulatus;* from the class of the *Chilopoda*, for example *Geophilus carpophagus* and *Scutigera* spec.;

from the class of the *Symphyla*, for example *Scutigerella immaculate;* from the order of the *Thysanura*, for example *Lepisma saccharina;* from the order of the *Collembola*, for example *Onychiurus armatus;* from the order of the *Orthoptera*, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the *Dermaptera*, for example *Forficula auricularia;* from the order of the *Isoptera*, for example *Reticulitermes* spp.;

from the order of the *Anoplura*, for example *Phylloxera vastatrix, Pemphigus* spp., *Pediculus humanus corporis, Haematopinus* spp. and *Linognathus* spp.;

from the order of the *Mallophaga*, for example *Trichodectes* spp. and *Damalinea* spp.;

from the order of the *Thysanoptera*, for example *Hercinothrips femoralis* and *Thrips tabaci;* from the order of the *Heteroptera*, for example *Eurygaster* spp., *Dysdercus intermedius, Piesma quadrata, Cimex lectularius, Rhodnius prolixus* and *Triatoma* spp.;

from the order of the *Homoptera*, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.;

from the order of the *Lepidoptera*, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the *Coleoptera*, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agrioties* spp., *Conoderus* spp., *Melolontha melolontha, Amphimallon solstitialis* and *Costelytra zealandica;* from the order of the *Hymenoptera*, for example *Diprion* spp., *Hoplocampa* spp., *Lasius* spp., *Monomorium pharaonis* and *Vespa* spp.;

from the order of the *Diptera*, for example *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa;* from the order of the *Siphonaptera*, for example *Xenopsylla cheopis* and *Ceratophyllus* spp.

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e., plant compatible or herbicidally inert) pesticide diluents or extenders, i.e. diluents, carriers or extenders of the type usable in conventional pesticide formulations or compositions, e.g., conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g., dichlorodifluoromethane and trichlorofluoromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols, (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, corn cobs and tabacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other insecticides and acaricides, or fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

As concerns commercially marketed preparations, these generally contemplate carrier composition mixtures in which the active compound is present in an amount substantially between about 0.1-95% by weight, and preferably 0.5-90% by weight, of the mixture, whereas carrier composition mixtures suitable for direct application or field application generally contemplate those in which the active compound is present in an amount substantially between about 0.0000001-100, preferably 0.01-10%, by weight of the mixture. Thus, the present invention contemplates overall compositions which comprise mixture of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.001-95%, and preferably 0.01-95% by weight of the mixture.

The active compounds can also be used in accordance with the well known ultra-low-volume process with good success, i.e., by applying such compound if normally a liquid, or by applying a liquid composition containing the same, via very effective atomizing equipment, in finely divided form, e.g. average particle diameter of from 50–100 microns, or even less, i.e., mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. arthropods such as insects and acarids, which comprises applying to at least one of correspondingly (a) such insects (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The process of the present invention is illustrated by the following preparative example:

EXAMPLE 1 a. $C_2H_5O-CH_2-CO-CH_2-CO-OC_2H_5$

1st stage 72 g (1 mol) of chlorine were passed into a solution of 84 g (1 mol) of diketene in dry carbon tetrachloride at $-20°$ C and the reaction solution was then added dropwise, while stirring, to 200 ml of ethanol, during which addition the temperature was not allowed to rise above 0° C. The solvent was then stripped off in vacuo on a rotary evaporator and the residue was distilled. 155 g (94% of theory) of γ-chloroacetoacetic acid ethyl ester of boiling point 90° C/7 mm Hg were obtained.

2nd stage 2.2 mol of sodium ethylate in ethanol — prepared from 55.2 g (2.2 mol) of sodium and 500 ml of ethanol — were diluted with 500 ml of tetrahydrofuran and 164.5 g (1 mol) of γ-chloroacetoacetic acid ethyl ester were then poured in, at room temperature, in such a way that the reaction temperature rose to 50° C. The mixture was then allowed to cool to room temperature, 72 g (1.2 mol) of glacial acetic acid were added, the solvent was evaporated off in vacuo on a rotary evaporator, the residue was shaken with 250 ml of water and extracted twice with 250 ml of methylene chloride at a time, and the combined organic phases were dried over magnesium sulphate. The solvent was distilled off and after distillation of the residue 123.7 g (71% of theory) of γ-ethoxyacetoacetic acid ethyl ester of boiling point 75° C/3 mm Hg were obtained.

γ-Methoxyacetoacetic acid methyl ester was prepared analogously; yield 63% of theory; boiling point: 76° C/7 mm Hg.

b. n—$C_3H_7S$—$CH_2$—CO—$CH_2$—CO—$OC_2H_5$ 367 g (2.3 mol) of bromine were added dropwise over the course of 90 minutes, at 0° C, to a solution of 300 g (2.3 mol) of acetoacetic acid ethyl ester in 350 ml of ether, the mixture was then stirred for a further hour at room temperature, 500 ml of water were added while cooling with ice, the phases were separated and the ether phase was washed once with 100 ml of a 10% strength sodium bicarbonate solution. The ether phase was then dried over magnesium sulphate and added dropwise, at room temperature, to an ethanolic solution of 2 mol of sodium propylmercaptide - prepared from 46 g (2 mol) of sodium, 600 g of ethanol and 152 g (2 mol) of propyl mercaptan — after which the reaction was stirred for a further hour at room temperature and then extracted by shaking with 2 mol of sodium hydroxide solution (1 334 g of a 6% strength solution). The ether phase was discarded and the aqueous phase was acidified with concentrated hydrochloric acid to pH-2 and was then extracted by shaking 3 times with 300 ml of methylene chloride at a time. The combined organic phases were dired over magnesium sulphate, the solvent was stripped off and after distillation of the residue 200 g (50% of theory or γ-propylmercaptoacetoacetic acid ester of boiling point 85° C.0.7 mm Hg were obtained.

The following were prepared analogously:

|  | Yield: | Boiling point: |
|---|---|---|
| γ-methylmercaptoacetoacetic acid ester | 60% of theory | 105° C/2 mm Hg |
| γ-ethylmercaptoacetoacetic acid ester | 56% of theory | 99° C/1 mm Hg | s1

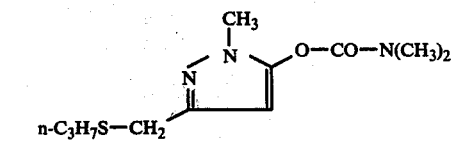

c) n-$C_3H_7S$—$CH_2$ 9.2 g (0.2 mol) of methylhydrazine were added dropwise to a solution of 38 g (0.2 mol) of γ-propylmercaptoacetoacetic acid methyl ester in 150 ml of ethanol in such a way that the temperature rose to 55°–60° C. After stirring the reaction solution for a further hour at 60° C, the solvent was completely distilled off in vacuo on a rotary evaporator and the crystalline residue was stirred with 250 ml of ether, filtered off and dried. 24 g (65% of theory) of 1-methyl-3-n-propylthiomethyl-5-hydroxy-pyrazole remained in the form of colorless crystals of melting point 108°–110° C.

The followng starting compounds of the formula

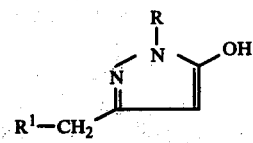

(II)

could be prepared analogously (s means starting compound):

Table 1

| S No. | R | $R^1$ | Yield (% of theory) | Physical data (refractive index; melting point ° C) |
|---|---|---|---|---|
| s 2 | H | $CH_3O$ | 86 | 95–98 |
| s 3 | $CH_3$ | $CH_3O$ | 73 | 87 |
| s 4 | $CH_3$ | $C_2H_5O$ | 68 | 97 |
| s 5 | iso-$C_3H_7$ | $CH_3O$ | 87 | $n_D^{23}$:1.4900 |
| s 6 | ⌬ | $C_2H_5O$ | 98 | $n_D^{23}$:1.5310 |
| s 7 | —$CH_2$—$CH_2$—CN | $CH_3O$ | 88 | 78–80 |
| s 8 | iso-$C_3H_7$ | n-$C_3H_7S$ | 80 | 91 |
| s 9 | $CH_3$ | $C_2H_5S$ | 83 | 114 |
| s 10 | $CH_3$ | $CH_3S$ | 86 | 130 |
| s 11 | —$CH_2$—$CH_2$—CN | $CH_3S$ | 56 | 98 |
| s 12 | $C_3H_7$-iso | $SCH_3$ | 97 | 98 |
| s 13 | $C_3H_7$-iso | $SC_3H_7$-iso |  |  |
| s 14 | $C_3H_7$-iso | $SC_4H_9$-sec. |  |  |
| s 15 | $C_2H_5$ | $SCH_3$ |  |  |
| s 16 | $C_2H_5$ | $SC_2H_5$ |  |  |
| s 17 | $C_3H_7$-n | $SCH_3$ |  |  |
| s 18 | $C_3H_7$-n | $SC_2H_5$ |  |  |
| s 19 | $C_4H_9$-n | $SCH_3$ |  |  |
| s 20 | $C_4H_9$-n | $SC_2H_5$ |  |  |
| s 21 | $C_4H_9$-iso | $SCH_3$ |  |  |
| s 22 | $C_4H_9$-iso | $SC_2H_5$ |  |  |
| s 23 | $C_4H_9$-sec. | $SCH_3$ |  |  |
| s 24 | $C_4H_9$-sec. | $SC_2H_5$ |  |  |
| s 25 | $C_4H_9$-tert. | $SCH_3$ |  |  |
| s 26 | $C_4H_9$-tert. | $SC_2H_5$ |  |  |
| s 27 | $CH_2$—$C(CH_3)_3$ | $SCH_3$ |  |  |
| s 28 | $CH(C_2H_5)_2$ | $SCH_3$ |  |  |
| s 29 | $C_3H_7$-iso | $OC_2H_5$ |  |  |
| s 30 | $C_3H_7$-iso | $OC_3H_7$-iso |  |  |
| s 31 | $C_2H_5$ | $OCH_3$ |  |  |
| s 32 | $C_2H_5$ | $OC_2H_5$ |  |  |
| s 33 | $C_3H_7$-n | $OCH_3$ |  |  |
| s 34 | $C_3H_7$-n | $OC_2H_5$ |  |  |
| s 35 | $C_4H_9$-n | $OCH_3$ |  |  |
| s 36 | $C_4H_9$-n | $OC_2H_5$ |  |  |
| s 37 | $C_4H_9$-iso | $OCH_3$ |  |  |
| s 38 | $C_4H_9$-iso | $OC_2H_5$ |  |  |
| s 39 | $C_4H_9$-sec. | $OCH_3$ |  |  |
| s 40 | $C_4H_9$-sec. | $OC_2H_5$ |  |  |
| s 41 | $C_4H_9$-tert. | $OCH_3$ |  |  |
| s 42 | $C_4H_9$-tert. | $OC_2H_5$ |  |  |
| s 43 | —$CH_2$—$C(CH_3)_3$ | $OCH_3$ |  |  |
| s 44 | $CH(C_2H_5)_2$ | $OCH_3$ |  |  |
| s 45 | $C_3H_7$-iso | $OC_3H_7$-n |  |  |
| s 46 | $C_3H_7$-iso | $SC_3H_7$-n |  |  |
| s 47 | $C_3H_7$-iso | $SC_2H_5$ | 63 | 88 | b)

$$\underset{n\text{-}C_3H_7S-CH_2}{\text{pyrazole with } CH_3 \text{ on N, } O\text{-}CO\text{-}N(CH_3)_2}$$ (I)

A suspension of 9.3 g (50 mmol) of 1-methyl-3-n-propylthiomethyl-5-hydroxy-pyrazole, 8.4 g (60 mmol) of ground potassium carbonate and 200 ml of acetonitrile was stirred for 1 hour at 50° C and then cooled to room temperature, and 5.4 g (50 mmol) of N,N-dimethylcarbamic acid chloride were then added. After stirring the reaction solution for one hour at 50° C, 200 ml of water were added and the mixture was extracted by shaking with 300 ml of toluene. The organic phase was dried over magnesium sulphate and filtered and the solvent was stripped off in vacuo on a rotary evaporator. 12 g (94% of theory) of N,N-dimethyl-O-[1-methyl-3-n-propylthiomethyl-pyrazol-5-yl]-carbamic acid ester were left in the form of a yellow oil havng a refractive index $n_D^{23}$ of 1.5095.

The following compounds of the formula

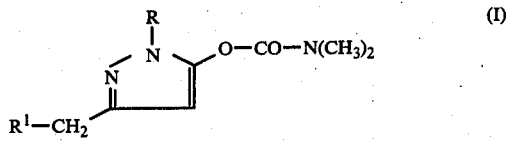

could be prepared analogously:

Table 2

| Compound No. | R | $R^1$ | Yield (% of theory) | Physical data (refractive index: melting point °C) |
|---|---|---|---|---|
| 2 | $C_3H_7$-iso | $OCH_3$ | 83 | $n_D^{23}$:1.5431 |
| 3 | | $OC_2H_5$ | 90 | $n_D^{23}$:1.5442 |
| 4 | H | $OCH_3$ | 84 | $n_D^{23}$:1.4909 |
| 5 | $CH_3$ | $OCH_3$ | 92 | $n_D^{23}$:1.4914 |
| 6 | $CH_3$ | $OC_2H_5$ | 97 | $n_D^{22}$:1.4886 |
| 7 | $-CH_2-CH_2-CN$ | $OCH_3$ | 87 | $n_D^{23}$:1.5005 |
| 8 | $CH_3$ | $SCH_3$ | 70 | $n_D^{23}$:1.5299 |
| 9 | $-CH_2-CH_2-CN$ | $SCH_3$ | 61 | $n_D^{23}$:1.5280 |
| 10 | $-CH_3$ | $SC_2H_5$ | 90 | 40 |
| 11 | $C_3H_7$-iso | $SC_2H_5$ | 73 | 54 |
| 12 | $C_3H_7$-iso | $SCH_3$ | 65 | 65 |
| 13 | $C_3H_7$-iso | $SC_3H_7$-iso | | |
| 14 | $C_3H_7$-iso | $SC_4H_9$-sec. | | |
| 15 | $C_2H_5$ | $SCH_3$ | | |
| 16 | $C_2H_5$ | $SC_2H_5$ | | |
| 17 | $C_3H_7$-n | $SCH_3$ | | |
| 18 | $C_3H_7$-n | $SC_2H_5$ | | |
| 19 | $C_4H_9$-n | $SCH_3$ | | |
| 20 | $C_4H_9$-n | $SC_2H_5$ | | |
| 21 | $C_4H_9$-iso | $SCH_3$ | | |
| 22 | $C_4H_9$-iso | $SC_2H_5$ | | |
| 23 | $C_4H_9$-sec. | $SCH_3$ | | |
| 24 | $C_4H_9$-sec. | $SC_2H_5$ | | |
| 25 | $C_4H_9$-tert. | $SCH_3$ | | |
| 26 | $C_4H_9$-tert. | $SC_2H_5$ | | |
| 27 | $CH_2-C(CH_3)_3$ | $SCH_3$ | | |
| 28 | $CH(C_2H_5)_2$ | $SCH_3$ | | |
| 29 | $C_3H_7$-iso | $OC_2H_5$ | | |
| 30 | $C_3H_7$-iso | $OC_3H_7$-iso | | |
| 31 | $C_2H_5$ | $OCH_5$ | | |
| 32 | $C_2H_5$ | $OC_2H_5$ | | |
| 33 | $C_3H_7$-n | $OCH_3$ | | |
| 34 | $C_3H_7$-n | $OC_2H_5$ | | |

The insecticidal activity of the compounds of this invention is illustrated by the following examples wherein the compounds according to the present invention are each identified by the number (given in brackets) from the preparative example hereinabove.

The known comparison compounds are identified as follows:

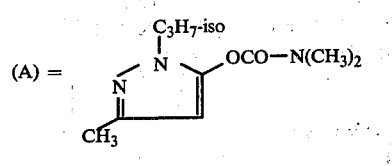

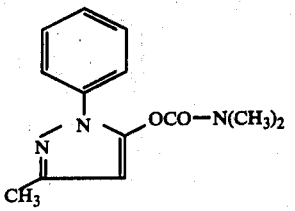

EXAMPLE 2

Myzus test (contact action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (brassica oleracea) which had been heavily infested with peach aphids (*Myzus persicae*) were sprayed with the preparation of the active compound until dripping wet.

After the specified periods of time, the degree of destruction was determined as a percentage: 100% meant that all of the aphids were killed whereas 0% meant that none of the aphids were killed.

The active compounds, the concentrations of the active compounds, the evaluation times and the results can be seen from the following table:

TABLE 3

| (insects which damage plants) Myzus test | | |
|---|---|---|
| Active compound | Active compound concentration in % | Degree of destruction in % after 1 day |
| (A) | 0.1 | 100 |
| | 0.01 | 0 |
| (B) | 0.1 | 98 |
| | 0.01 | 0 |
| (5) | 0.1 | 100 |
| | 0.01 | 100 |
| (8) | 0.1 | 100 |
| | 0.01 | 100 |
| (6) | 0.1 | 100 |
| | 0.01 | 98 |
| (10) | 0.1 | 100 |
| | 0.01 | 100 |
| (1) | 0.1 | 100 |
| | 0.01 | 98 |
| (2) | 0.1 | 100 |
| | 0.01 | 100 |
| (7) | 0.1 | 100 |
| | 0.01 | 100 |
| (9) | 0.1 | 100 |
| | 0.01 | 100 |

EXAMPLE 3

Phaedon larvae test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dripping wet and were then infested with mustard beetle larvae (*Phaedon cochleariae*).

After the specified periods of time, the degree of destruction was determined in %: 100% meant that all of the beetle larvae had been killed whereas 0% meant that none of the beetle larvae had been killed.

The active compounds, the concentrations of the active compounds, the evaluation times and the results can be seen from the following table:

Table 4

| | (insects which damage plants) *Phaedon* larvae test | |
|---|---|---|
| Active compound | Active compound concentration in % | Degree of destruction in % after 3 days |
| (A) | 0.1 | 60 |
| | 0.01 | 0 |
| (5) | 0.1 | 100 |
| | 0.01 | 100 |

EXAMPLE 4

Root-systemic action

Test insect: Myzus persicae

Solvent: 3 parts by weight of acetone

Emulsifier: 1 part by weight of alkylaryl polyglycol ether

To produce a suitable preparation of active compound, 1 part by weight of active compound was mixed with the stated amount of solvent, the stated amount of emulsifier was added and the concentrate was diluted with water to the desired concentration The preparation of active compound was intimately mixed with the soil. The concentration of the active compound in the preparation was of practically no importance; only the amount of active compound per unit volume of soil, which is given hereinafter in ppm (= mg/1), was decisive. The treated soil was filled into pots and these were planted with cabbage (Brassica oleracea). The active compound could in this way be taken up from the soil by the plant roots and be transported into the leaves.

To demonstrate the root-systemic effect, only the leaves were infested with the above-mentioned test insects after 7 days. After a further 2 days, the results were evaluated by counting or estimating the dead insects. The root-systemic action of the active compound was deduced from the desctruction data. It was 100% when all of the test insects had been killed and 0% when just as many test insects ere still alive as in the case of the untreated control.

The active compounds, the amounts used and the results can be seen from the following table:

Table 5

| | (root-systemic action) *Myzus persicae* |
|---|---|
| Active compounds | Degree of destruction at an active compound concentration of 20 ppm |
| (B) | 0 |
| (10) | 100 |
| (8) | 100 |
| (6) | 100 |
| (5) | 100 |
| (1) | 100 |
| (7) | 100 |
| (2) | 100 |
| (4) | 100 |

EXAMPLE 5

Test with parasitic fly larvae

Solvent: 35 parts by weight of ethylene polyglycol monomethyl ether

Emulsifier: 35 parts by weight of nonylphenol polyglycol ether

To produce a suitable preparation of active compound, 30 parts by weight of the active substance in question were mixed with the stated amount of solvent which contained the above-mentioned proportion of emulsifier and the concentrate thus obtained was diluted with water to the desired concentration.

About 20 fly larvae (*Lacilia cuprina*) were introduced into a test tube which contained approx. 2 ml of horse muscle. 0.5 ml of the preparation of active compound was applied to this horse meat. After 24 hours, the degree of destruction in % was determined. 100% meant that all of the larve had been killed and 0% meant that none of the larvae had been killed.

The active compounds, the concentrations of the active compounds and the results can be seen from the table which follows:

Table 6

| | Parasitic fly larvae test/ *Lucilia cuprina* res. | |
|---|---|---|
| Active compound | Active compound concentration in ppm | Destructive action in % |
| (5) | 1,000 | 100 |
| | 100 | 100 |
| | 10 | 0 |
| (4) | 1,000 | 100 |
| | 300 | 100 |
| | 100 | 100 |
| | 30 | 100 |
| | 10 | — |

It will be appreciated that the instant specification and examples are set forth by way of illustration and not limitation, and that various modifications and changes may be made without departing from the spirit and scope of the present invention.

What is claimed is:

1. An N,N-dimethyl-O-[3-substitutedmethyl)-pyrazol-5yl]-carbamic acid ester of the formula

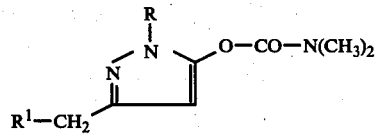

in which

R is hydrogen, alkyl with 1 to 5 carbon atoms, cyanoalkyl with 1 to 4 carbon atoms in the alkyl radical or phenyl, and Rhu 1 is alkoxy or alkylthio each with 1 to 6 carbon toms.

2. An ester according to claim 1, wherein such ester is N,N-dimethyl-O-[1-methyl-3-n-propylthiomethyl-pyrazol-5-yl]-carbamic acid ester of the formula

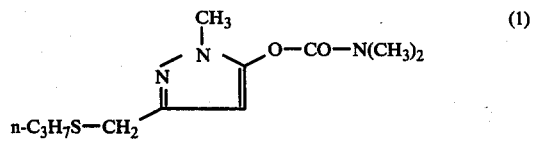

(1)

3. An ester ester according to claim 1, wherein such ester is N,N-dimethyl-O-[1-isopropyl-3-methoxymethyl-pyrazol-5-yl]-carbamic acid ester of the formula

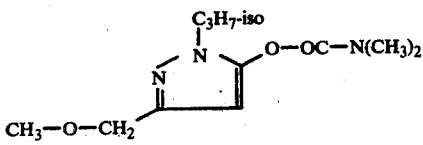

4. An ester according to claim 1, wherein such ester is N,N-dimethyl-O-[1-methyl-3-methylthiomethyl-pyrazol-5-yl]-carbamic acid ester of the formula

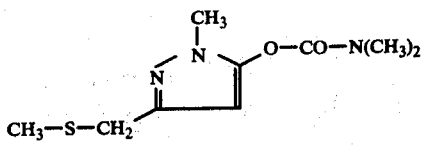

5. An arthropodicidal composition containing as active ingredient an arthropodicidally effective amount of a compound according to claim 1 in admixture with a diluent.

6. A method of combating arthropods which comprises applying to the arthropods, or to a habitat thereof, an arthropodicidally effective amount of a compound according to claim 1.

7. The method according to claim 6, wherein said compound is applied to a domesticated animal.

8. The method according to claim 6, in which said compound is
N,N-dimethyl-O-[1-methyl-3-n-propylthiomethyl-pyrazol-5-yl]-carbamic acid ester,
N,N-dimethyl-O-[1-isopropyl-3-methoxymethyl-pyrazol-5yl]-carbamic acid ester, or
N,N-dimethyl-O-[1-methyl-3-methylthiomethyl-pyrazol-5-yl]-carbamic acid.

* * * * *

UNITED STATES PATENT AND TRADEMARK OFFICE
CERTIFICATE OF CORRECTION

PATENT NO. : 4,126,690

DATED : Nov. 21, 1978

INVENTOR(S) : Fritz Maurer et al

It is certified that error appears in the above-identified patent and that said Letters Patent are hereby corrected as shown below:

Column 14, Line 57  Delete "Rhu 1" and insert $--R^1--$.

Signed and Sealed this

Nineteenth Day of May 1981

[SEAL]

Attest:

RENE D. TEGTMEYER

Attesting Officer   Acting Commissioner of Patents and Trademarks